United States Patent
Watanabe et al.

(10) Patent No.: US 10,737,999 B2
(45) Date of Patent: Aug. 11, 2020

(54) 1-HALOALKADIENE AND A PROCESS FOR PREPARING THE SAME AND A PROCESS FOR PREPARING (9E, 11Z)-9,11-HEXADECADIENYL ACETATE

(71) Applicant: SHIN-ETSU CHEMICAL CO., LTD., Tokyo (JP)

(72) Inventors: Tomohiro Watanabe, Niigata (JP); Yuki Miyake, Niigata (JP); Takeshi Kinsho, Niigata (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 16/388,156

(22) Filed: Apr. 18, 2019

(65) Prior Publication Data

US 2019/0322614 A1   Oct. 24, 2019

(30) Foreign Application Priority Data

Apr. 18, 2018   (JP) .................................. 2018-079776

(51) Int. Cl.
| | |
|---|---|
| *C07C 67/03* | (2006.01) |
| *C07C 17/263* | (2006.01) |
| *C07C 29/124* | (2006.01) |
| *C07C 21/04* | (2006.01) |
| *C07C 33/02* | (2006.01) |
| *C07C 69/587* | (2006.01) |

(52) U.S. Cl.
CPC .......... *C07C 67/03* (2013.01); *C07C 17/2635* (2013.01); *C07C 29/124* (2013.01); *C07C 21/04* (2013.01); *C07C 33/02* (2013.01); *C07C 69/587* (2013.01)

(58) Field of Classification Search
CPC ... C07C 67/03; C07C 17/2635; C07C 29/124; C07C 21/04; C07C 33/02; C07C 69/587

USPC ........................................................ 554/224
See application file for complete search history.

(56) References Cited

FOREIGN PATENT DOCUMENTS

EP          87400592.9 A1    10/1987

OTHER PUBLICATIONS

Chemical Abstracts Service, 2010, Stefan Ries: "An Approach to the Total Synthesis of Pseudodistomine C and E : A New Synthetic Pathway", XP002793130, Database accession No.*
Chemreact abstr of Ries.*
European Search Report for Application 19167818.4, dated Sep. 10, 2019.
Millar, Jocelyn G. et al., "Sex Attractant Pheromone of the Pecan Nut Casebearer (Lepidoptera: Pyralidaw)"; Bioorganic & Medicinal Chemistry, vol. 4, No. 3, pp. 331-339 (1996).
XP-002793130 File Caplus.
XP-002793136; Tetrahedron Letters No. 1, pp. 121-124, 1977. Pergamon Press. Printed in Great Britain.
Harris, M. K. et al., *A New Pheromone Race of Acrobasis nuxvorella* (*Lepidoptera: Pyralidae*), Journal of Economic Entomology, vol. 101, No. 3 (2008) 769-776.
Millar, J. G. et al., Sex Attractant Pheromone of the Pecan Nut Casebearer (*Lepidoptera: Pyralidae*), Bioorganic & Medicinal Chemistry, vol. 4, No. 3 (1996) 331-339.

* cited by examiner

*Primary Examiner* — Deborah D Carr
(74) *Attorney, Agent, or Firm* — Rimon, P.C.

(57) ABSTRACT

A process to prepare (9E,11Z)-9,11-hexadecadienyl acetate with a good yield and high purity of the general formula (1): $CH_3-(CH_2)_3-CH=CH-CH=CH-(CH_2)_a-X$.=The process includes a step of conducting a Wittig reaction between a haloalkenal of the general formula (2): $OHC-CH=CH-(CH_2)_a-X$, and a triarylphosphonium pentylide of the general formula (3): $CH_3-(CH_2)_3-CH^--P^+Ar_3$, to obtain the 1-haloalkadiene, and the use of a (7E,9Z)-1-halo-7,9-tetradecadiene obtained by the process for a process of preparing (9E, 11Z)-9,11-hexadecadienyl acetate.

4 Claims, No Drawings

1-HALOALKADIENE AND A PROCESS FOR PREPARING THE SAME AND A PROCESS FOR PREPARING (9E, 11Z)-9,11-HEXADECADIENYL ACETATE

FIELD

The present invention relates to a process for preparing (9E,11Z)-9,11-hexadecadienyl acetate from a 1-haloalkadiene.

BACKGROUND

Pecan nut casebearer (*Acrobasis nuxvorella*) is a serious insect pest against pecans, which tunnels into pecan nuts and feeds in the nuts. The use of insecticides for pest control on the pecan nut casebearer may lead to outbreak of secondary insect pests, such as aphids, mites and leaf-miner flies, because the insecticides also kill natural enemies of such secondary insect pests. Therefore, a large hope is placed on mating disruption using a sex pheromone.

(9E,11Z)-9,11-Hexadecadienal and (9E,11Z)-9,11-hexadecadienyl acetate were identified as components of natural sex pheromones of the pecan nut casebearer (Non-Patent Literatures 1 (J. G. Millar et al., Bioorg. Med. Chem. 1996, 4, 331-339) and 2 (M. K. Harris et al., J. Econ. Entomol. 2008, 101, 769-776)). Harris et al. describes a process for preparing (9E,11Z)-9,11-hexadecadienyl acetate, in which (1E)-1-chloro-1-octen-3-yne, which has been obtained by the Sonogashira coupling of (E)-1,2-dichloroethene with 1-hexyne, is subjected to the Kochi-Fürstner coupling with 1-(tetrahydropyranyloxy)-8-bromooctane derived from 1,8-octanediol to obtain (9E)-1-(tetrahydropyranyloxy)-9-hexadecen-11-yne, followed by hydroboration and subsequent protonation, removal of a protecting tetrahydropyranyl (THP) group for the hydroxy group, and acetylation reaction (Non-Patent Literature 2).

SUMMARY

However, the process described in Non-Patent Literature 2 requires expensive (E)-1,2-dichloroethene as one of the starting materials, and expensive dichlorobis(triphenylphosphine) palladium for the Sonogashira coupling. The yield of the process is as low as 62%, which makes the process unsuitable for the industrial production. Further, it cannot be carried out in a usual reaction facility, because the hydroboration is carried out at −20° C. In addition, because THP group is used as a protecting group, two additional steps are required for the protection and deprotection of hydroxyl group. This is undesirable for industrial practice, because of the increased number of steps. Furthermore, the deprotection from an ether-type protecting group such as THP group is an equilibrium reaction, so that some of the protection remains even after the deprotection step, which may lead to a decreased yield. For example, the overall yield of (9E,11Z)-9,11-hexadecadienyl acetate is significantly so low as 32% in Non-Patent Literature 2.

As a result of intensive studies to solve the problems described above, the present inventors have discovered a 1-haloalkadiene useful as an intermediate and have found that (9E,11Z)-9,11-hexadecadienyl acetate can be produced with a high yield and a high purity, without using any protection or deprotection reaction, and without a need for a special facility, from a (7E,9Z)-1-halo-7,9-tetradecadiene or (9E,11Z)-1-halo-9,11-hexadecadiene, and have completed the present invention.

According to one aspect of the invention, there is provided a process for preparing a 1-haloalkadiene of the following general formula (1):

$$CH_3—(CH_2)_3—CH=CH—CH=CH—(CH_2)_a—X \quad (1),$$

wherein X is a halogen atom, and a is an integer of from 3 to 15, said process comprising at least a step of:

conducting a Wittig reaction between a haloalkenal of the following general formula (2):

$$OHC—CH=CH—(CH_2)_a—X \quad (2),$$

wherein X and a are as defined above for the general formula (1), and a triarylphosphonium pentylide of the following general formula (3):

$$CH_3—(CH_2)_3—CH^−—P^+Ar_3 \quad (3),$$

wherein Ar may be the same or different at each occurrence and is an aryl group having 6 or 7 carbon atoms, to obtain the 1-haloalkadiene.

According to another aspect of the invention, there is provided a process for preparing (9E,11Z)-9,11-hexadecadienyl acetate of the following formula (7):

(7)

said process comprising at least steps of:

conducting the foregoing process for preparing the 1-haloalkadiene to prepare a (7E,9Z)-1-halo-7,9-tetradecadiene of the following general formula (1-1):

(1-1)

subjecting a (7E,9Z)-7,9-tetradecadienyl magnesium halide derived from the (7E,9Z)-1-halo-7,9-tetradecadiene (1-1) to an addition reaction with ethylene oxide to obtain (9E,11Z)-9,11-hexadecadienol of the following formula (6):

(6)

and conducting an acetylation reaction of (9E,11Z)-9,11-hexadecadienol (6) with an acylating agent to obtain (9E,11Z)-9,11-hexadecadienyl acetate.

According to still another aspect of the invention, there is provided a process for preparing a 1-haloalkadiene of the following general formula (1A):

$$CH_3—(CH_2)_3—CH=CH—CH=CH—(CH_2)_{a'}—X \quad (1A),$$

wherein X is a halogen atom, and a' is an integer of from 6 to 15, said process comprising at least a step of:

conducting a coupling reaction of an alkadienyl magnesium halide derived from a 1-haloalkadiene of the following general formula (4):

$$CH_3—(CH_2)_3—CH=CH—CH=CH—(CH_2)_c—X^1 \quad (4),$$

wherein $X^1$ is a halogen atom, and c is an integer of 3 or of from 5 to 12, with a dihaloalkane of the following general formula (5):

$$X—(CH_2)_d—X \quad (5),$$

wherein X may be the same or different at each occurrence and is a halogen atom, and d is an integer of from 3 to 12, with a proviso that a sum of c and d is from 6 to 15, to obtain the 1-haloalkadiene defined above.

According to a still another aspect of the invention, there is provided a process for preparing (9E,11Z)-9,11-hexadecadienyl acetate of the following formula (7):

(7)

said process comprising at least steps of:

conducting the foregoing process for preparing the 1-haloalkadiene to prepare a (9E,11Z)-1-halo-9,11-hexadecadiene of the following general formula (1-2):

(1-2)

and substituting the halogen atom in the (9E,11Z)-1-halo-9,11-hexadecadiene (1-2) with an acetoxy group to obtain (9E,11Z)-9,11-hexadecadienyl acetate.

According to a further aspect of the invention, there is provided a 1-haloalkadiene of the general formula (1) shown above.

The 1-haloalkadiene according to the invention is useful as a synthetic intermediate in the preparation of an organic compound having a conjugated diene structure. According to the invention, (9E,11Z)-9,11-hexadecadienyl acetate can be produced with a high yield and a high purity, without using expensive reagents, and without a need to use any special facility.

DETAILED DESCRIPTION

First, here described is the 1-haloalkadiene of the following general formula (1):

$$CH_3—(CH_2)_3—CH=CH—CH=CH—(CH_2)_a—X \quad (1)$$

In the general formula (1), X is a halogen atom, examples of which preferably include chlorine, bromine and iodine atoms, and a is an integer of from 3 to 15, preferably from 3 to 8, more preferably from 5 to 7.

Illustrative geometrical isomers of the 1-haloalkadiene (1) include (E,E), (E,Z), (Z,E) and (Z,Z) isomers.

Examples of the 1-haloalkadiene (1) include a 1-halo-4,6-undecadiene (a=3), a 1-halo-5,7-dodecadiene (a=4), a 1-halo-6,8-tridecadiene (a=5), a 1-halo-7,9-tetradecadiene (a=6), a 1-halo-8,10-pentadecadiene (a=7), a 1-halo-9,11-hexadecadiene (a=8), a 1-halo-10,12-heptadecadiene (a=9), a 1-halo-11,13-octadecadiene (a=10), a 1-halo-12,14-nonadecadiene (a=11), a 1-halo-13,15-eicosadiene (a=12), a 1-halo-14,16-heneicosadiene (a=13), a 1-halo-15,17-docosadiene (a=14), and a 1-halo-16,18-tricosadiene (a=15).

Specific examples of the 1-halo-4,6-undecadiene include (4E,6E)-1-chloro-4,6-undecadiene, (4E,6Z)-1-chloro-4,6-undecadiene, (4Z,6E)-1-chloro-4,6-undecadiene, (4Z,6Z)-1-chloro-4,6-undecadiene, (4E,6E)-1-bromo-4,6-undecadiene, (4E,6Z)-1-bromo-4,6-undecadiene, (4Z,6E)-1-bromo-4,6-undecadiene, (4Z,6Z)-1-bromo-4,6-undecadiene, (4E,6E)-1-iodo-4,6-undecadiene, (4E,6Z)-1-iodo-4,6-undecadiene, (4Z,6E)-1-iodo-4,6-undecadiene, and (4Z,6Z)-1-iodo-4,6-undecadiene.

Specific examples of the 1-halo-5,7-dodecadiene include (5E,7E)-1-chloro-5,7-dodecadiene, (5E,7Z)-1-chloro-5,7-dodecadiene, (5Z,7E)-1-chloro-5,7-dodecadiene, (5Z,7Z)-1-chloro-5,7-dodecadiene, (5E,7E)-1-bromo-5,7-dodecadiene, (5E,7Z)-1-bromo-5,7-dodecadiene, (5Z,7E)-1-bromo-5,7-dodecadiene, (5Z,7Z)-1-bromo-5,7-dodecadiene, (5E,7E)-1-iodo-5,7-dodecadiene, (5E,7Z)-1-iodo-5,7-dodecadiene, (5Z,7E)-1-iodo-5,7-dodecadiene, and (5Z,7Z)-1-iodo-5,7-dodecadiene.

Specific examples of the 1-halo-6,8-tridecadiene include (6E,8E)-1-chloro-6,8-tridecadiene, (6E,8Z)-1-chloro-6,8-tridecadiene, (6Z,8E)-1-chloro-6,8-tridecadiene, (6Z,8Z)-1-chloro-6,8-tridecadiene, (6E,8E)-1-bromo-6,8-tridecadiene, (6E,8Z)-1-bromo-6,8-tridecadiene, (6Z,8E)-1-bromo-6,8-tridecadiene, (6Z,8Z)-1-bromo-6,8-tridecadiene, (6E,8E)-1-iodo-6,8-tridecadiene, (6E,8Z)-1-iodo-6,8-tridecadiene, (6Z,8E)-1-iodo-6,8-tridecadiene, and (6Z,8Z)-1-iodo-6,8-tridecadiene.

Specific examples of the 1-halo-7,9-tetradecadiene include (7E,9E)-1-chloro-7,9-tetradecadiene, (7E,9Z)-1-chloro-7,9-tetradecadiene, (7Z,9E)-1-chloro-7,9-tetradecadiene, (7Z,9Z)-1-chloro-7,9-tetradecadiene, (7E,9E)-1-bromo-7,9-tetradecadiene, (7E,9Z)-1-bromo-7,9-tetradecadiene, (7Z,9E)-1-bromo-7,9-tetradecadiene, (7Z,9Z)-1-bromo-7,9-tetradecadiene, (7E,9E)-1-iodo-7,9-tetradecadiene, (7E,9Z)-1-iodo-7,9-tetradecadiene, (7Z,9E)-1-iodo-7,9-tetradecadiene, and (7Z,9Z)-1-iodo-7,9-tetradecadiene.

Specific examples of the 1-halo-8,10-pentadecadiene include (8E,10E)-1-chloro-8,10-pentadecadiene, (8E,10Z)-1-chloro-8,10-pentadecadiene, (8Z,10E)-1-chloro-8,10-pentadecadiene, (8Z,10Z)-1-chloro-8,10-pentadecadiene, (8E,10E)-1-bromo-8,10-pentadecadiene, (8E,10Z)-1-bromo-8,10-pentadecadiene, (8Z,10E)-1-bromo-8,10-pentadecadiene, (8Z,10Z)-1-bromo-8,10-pentadecadiene, (8E,10E)-1-iodo-8,10-pentadecadiene, (8E,10Z)-1-iodo-8,10-pentadecadiene, (8Z,10E)-1-iodo-8,10-pentadecadiene, and (8Z,10Z)-1-iodo-8,10-pentadecadiene.

Specific examples of the 1-halo-9,11-hexadecadiene include (9E,11E)-1-chloro-9,11-hexadecadiene, (9E,11Z)-1-chloro-9,11-hexadecadiene, (9Z,11E)-1-chloro-9,11-hexadecadiene, (9Z,11Z)-1-chloro-9,11-hexadecadiene, (9E,11E)-1-bromo-9,11-hexadecadiene, (9E,11Z)-1-bromo-9,11-hexadecadiene, (9Z,11E)-1-bromo-9,11-hexadecadiene, (9Z,11Z)-1-bromo-9,11-hexadecadiene, (9E,11E)-1-iodo-9,11-hexadecadiene, (9E,11Z)-1-iodo-9,11-hexadecadiene, (9Z,11E)-1-iodo-9,11-hexadecadiene, and (9Z,11Z)-1-iodo-9,11-hexadecadiene.

Specific examples of the 1-halo-10,12-heptadecadiene include (10E,12E)-1-chloro-10,12-heptadecadiene, (10E,12Z)-1-chloro-10,12-heptadecadiene, (10Z,12E)-1-chloro-10,12-heptadecadiene, (10Z,12Z)-1-chloro-10,12-heptadecadiene, (10E,12E)-1-bromo-10,12-heptadecadiene, (10E,12Z)-1-bromo-10,12-heptadecadiene, (10Z,12E)-1-bromo-10,12-heptadecadiene, (10Z,12Z)-1-bromo-10,12-heptadecadiene, (10E,12E)-1-iodo-10,12-heptadecadiene, (10E,12Z)-1-iodo-10,12-heptadecadiene, (10Z,12E)-1-iodo-10,12-heptadecadiene, and (10Z,12Z)-1-iodo-10,12-heptadecadiene.

Specific examples of the 1-halo-11,13-octadecadiene include (11E,13E)-1-chloro-11,13-octadecadiene, (11E,13Z)-1-chloro-11,13-octadecadiene, (11Z,13E)-1-chloro-11,13-octadecadiene, (11Z,13Z)-1-chloro-11,13-octadecadiene, (11E,13E)-1-bromo-11,13-octadecadiene, (11E,13Z)-1-bromo-11,13-octadecadiene, (11Z,13E)-1-bromo-11,13-octadecadiene, (11Z,13Z)-1-bromo-11,13-octadecadiene, (11E,13E)-1-iodo-11,13-octadecadiene, (11E,13Z)-1-iodo-11,13-octadecadiene, (11Z,13E)-1-iodo-11,13-octadecadiene, and (11Z,13Z)-1-iodo-11,13-octadecadiene.

Specific examples of the 1-halo-12,14-nonadecadiene include (12E,14E)-1-chloro-12,14-nonadecadiene, (12E,14Z)-1-chloro-12,14-nonadecadiene, (12Z,14E)-1-chloro-12,14-nonadecadiene, (12Z,14Z)-1-chloro-12,14-nonadecadiene, (12E,14E)-1-bromo-12,14-nonadecadiene, (12E,14Z)-1-bromo-12,14-nonadecadiene, (12Z,14E)-1-bromo-12,14-nonadecadiene, (12Z,14Z)-1-bromo-12,14-nonadecadiene, (12E,14E)-1-iodo-12,14-nonadecadiene, (12E,14Z)-1-iodo-12,14-nonadecadiene, (12Z,14E)-1-iodo-12,14-nonadecadiene, and (12Z,14Z)-1-iodo-12,14-nonadecadiene.

Specific examples of the 1-halo-13,15-eicosadiene include (13E,15E)-1-chloro-13,15-eicosadiene, (13E,15Z)-1-chloro-13,15-eicosadiene, (13Z,15E)-1-chloro-13,15-eicosadiene, (13Z,15Z)-1-chloro-13,15-eicosadiene, (13E,15E)-1-bromo-13,15-eicosadiene, (13E,15Z)-1-bromo-13,15-eicosadiene, (13Z,15E)-1-bromo-13,15-eicosadiene, (13Z,15Z)-1-bromo-13,15-eicosadiene, (13E,15E)-1-iodo-13,15-eicosadiene, (13E,15Z)-1-iodo-13,15-eicosadiene, (13Z,15E)-1-iodo-13,15-eicosadiene, and (13Z,15Z)-1-iodo-13,15-eicosadiene.

Specific examples of the 1-halo-14,16-heneicosadiene include (14E,16Z)-1-chloro-14,16-heneicosadiene and (14E,16Z)-1-bromo-14,16-heneicosadiene.

Specific examples of the 1-halo-15,17-docosadiene include (15E,17Z)-1-chloro-15,17-docosadiene and (15E,17Z)-1-bromo-15,17-docosadiene.

Specific examples of the 1-halo-16,18-tricosadiene include (16E,18Z)-1-chloro-16,18-tricosadiene and (16E,18Z)-1-bromo-16,18-tricosadiene.

The 1-haloalkadiene (1) may be prepared by a Wittig reaction or a coupling reaction as will be described below.

First, the step of conducting a Wittig reaction between a haloalkenal of the general formula (2) and a triarylphosphonium pentylide of the general formula (3) to obtain the 1-haloalkadiene (1) will be described.

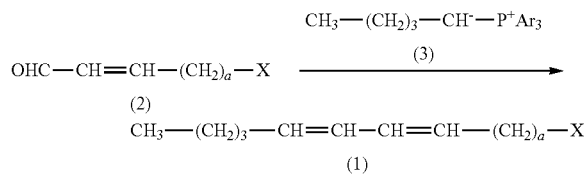

In the general formula (2), X is a halogen atom as defined for X in the general formula (1), and a is an integer of from 3 to 15, preferably from 3 to 8, more preferably from 5 to 7. In general formula (3), Ar may be the same or different at each occurrence and is an aryl group having 6 or 7 carbon atoms, such as phenyl and tolyl groups. In view of the ease of synthesis, phenyl group is preferred. More preferably, all of the three aryl groups are a phenyl group.

Illustrative geometrical isomers of the haloalkenal (2) include E and Z isomers.

Examples of the haloalkenal (2) include 6-halo-2-hexenal (b=3), 7-halo-2-heptenal (b=4), 8-halo-2-octenal (b=5), 9-halo-2-nonenal (b=6), 10-halo-2-decenal (b=7), 11-halo-2-undecenal (b=8), 12-halo-2-dodecenal (b=9), 13-halo-2-tridecenal (b=10), 14-halo-2-tetradecenal (b=11), 15-halo-2-pentadecenal (b=12), 16-halo-2-hexadecenal (b=13), 17-halo-2-heptadecenal (b=14), and 18-halo-2-octadecenal (b=15).

Specific examples of the 6-halo-2-hexenal include (2E)-6-chloro-2-hexenal, (2Z)-6-chloro-2-hexenal, (2E)-6-bromo-2-hexenal, (2Z)-6-bromo-2-hexenal, (2E)-6-iodo-2-hexenal, and (2Z)-6-iodo-2-hexenal.

Specific examples of the 7-halo-2-heptenal include (2E)-7-chloro-2-heptenal, (2Z)-7-chloro-2-heptenal, (2E)-7-bromo-2-heptenal, (2Z)-7-bromo-2-heptenal, (2E)-7-iodo-2-heptenal, and (2Z)-7-iodo-2-heptenal.

Specific examples of the 8-halo-2-octenal include (2E)-8-chloro-2-octenal, (2Z)-8-chloro-2-octenal, (2E)-8-bromo-2-octenal, (2Z)-8-bromo-2-octenal, (2E)-8-iodo-2-octenal, and (2Z)-8-iodo-2-octenal.

Specific examples of the 9-halo-2-nonenal include (2E)-9-chloro-2-nonenal, (2Z)-9-chloro-2-nonenal, (2E)-9-bromo-2-nonenal, (2Z)-9-bromo-2-nonenal, (2E)-9-iodo-2-nonenal, and (2Z)-9-iodo-2-nonenal.

Specific examples of the 10-halo-2-decenal include (2E)-10-chloro-2-decenal and (2E)-10-bromo-2-decenal.

Specific examples of the 11-halo-2-undecenal include (2E)-11-chloro-2-undecenal and (2E)-11-bromo-2-undecenal.

Specific examples of the 12-halo-2-dodecenal include (2E)-12-chloro-2-dodecenal and (2E)-12-bromo-2-dodecenal.

Specific examples of the 13-halo-2-tridecenal include (2E)-13-chloro-2-tridecenal and (2E)-13-bromo-2-tridecenal.

Specific examples of the 14-halo-2-tetradecenal include (2E)-14-chloro-2-tetradecenal and (2E)-14-bromo-2-tetradecenal.

Specific examples of the 15-halo-2-pentadecenal include (2E)-15-chloro-2-pentadecenal and (2E)-15-bromo-2-pentadecenal.

Specific examples of the 16-halo-2-hexadecenal include (2E)-16-chloro-2-hexadecenal and (2E)-16-bromo-2-hexadecenal.

Specific examples of the 17-halo-2-heptadecenal include (2E)-17-chloro-2-heptadecenal and (2E)-17-bromo-2-heptadecenal.

Specific examples of the 18-halo-2-octadecenal include (2E)-18-chloro-2-octadecenal and (2E)-18-bromo-2-octadecenal.

Any of a commercially available or synthesized haloalkenal (2) may be used.

Specific examples of the triarylphosphonium pentylide (3) include triphenylphosphonium pentylide and tritolylphosphonium pentylide Triphenylphosphonium pentylide is preferred for the economical reasons.

The triarylphosphonium pentylide (3) may be prepared by reacting the pentyltriarylphosphonium halide with a base in a solvent.

Examples of the pentyltriarylphosphonium halide to be used for the preparation of the triarylphosphonium pentylide (3) include pentyltriphenylphosphonium chloride, pentyltriphenylphosphonium bromide and pentyltriphenylphosphonium iodide. Pentyltriphenylphosphonium bromide and pentyltriphenylphosphonium iodide are preferred in view of the reactivity. Pentyltriarylphosphonium halides are commercially available or may be prepared by a conventional method.

The amount of the pentyltriarylphosphonium halide to be used may range preferably from 1.0 to 1.8 mol per mol of the haloalkenal (2) for completion of the reaction.

Examples of the base that may be used for the preparation of the triarylphosphonium pentylide (3) include metal alkoxides, such as sodium t-butoxide, potassium t-butoxide, sodium methoxide, potassium methoxide, sodium ethoxide and potassium ethoxide; an alkyllithium, such as n-butyllithium and t-butyllithium; and metal amides, such as lithium diisopropylamide and sodium bis(trimethylsilyl)amide. Metal alkoxides, such as potassium t-butoxide, sodium methoxide and sodium ethoxide, are preferred in view of the reactivity.

The amount of the base to be used may range preferably from 0.9 to 1.7 mol per mol of the haloalkenal (2) in view of the suppression of byproduct formation.

Examples of the solvent to be used for the preparation of the triarylphosphonium pentylide (3) include ether solvents, such as tetrahydrofuran, 4-methyltetrahydropyran and diethyl ether; hydrocarbon solvents, such as toluene, xylene and hexane; and polar solvents, such as N,N-dimethylformamide, N,N-dimethylacetamide, acetonitrile, dichloromethane and chloroform. Tetrahydrofuran is preferred in view of the reactivity. These solvents may be used alone or in combination.

The amount of the solvent to be used may vary, depending on a scale of the reaction system. It ranges preferably from 100 to 3,000 g per mol of the haloalkenal (2) in view of the reaction rate.

The reaction temperature during the preparation of the triarylphosphonium pentylide (3) may vary, depending on the type of the solvent to be used. It ranges preferably from −78 to 50° C., more preferably −20 to 25° C., in view of the reactivity.

The duration of the reaction for the preparation of the triarylphosphonium pentylide (3) may vary, depending on the type of the solvent or a scale of the reaction system. It ranges preferably from 0.1 to 10 hours.

The type and amount of the solvent to be used for the Wittig reaction may be the same as or different from those used for the preparation of the triarylphosphonium pentylide (3).

An optimum temperature for the Wittig reaction may vary, depending on the type of the solvent used. It ranges preferably from −78 to 25° C. In a case where the Wittig reaction is carried out in a Z-stereoselective manner, it is preferable to conduct the reaction at −78 to 10° C. In a case where the Wittig reaction is carried out in an E-stereoselective manner, on the other hand, it is preferable to conduct the reaction at −78 to −40° C., followed by the treatment of the resulting intermediate with a strong base, such as phenyllithium, thus under the conditions of the Schlosser Modification.

The duration of the Wittig reaction may vary, depending on a scale of the reaction system. It ranges preferably from 1 to 30 hours.

According to a preferable embodiment of the present process, an (E,Z)-1-haloalkadiene can be selectively prepared by conducting the Wittig reaction in a Z-stereoselective way using an E-isomer of the haloalkenal (2), which is an α,β-unsaturated aldehyde.

Next, there will be described the alternative procedures for preparing the 1-haloalkadiene (1A), that is, the coupling reaction of an alkadienyl magnesium halide, i.e., a Grignard reagent, derived from a 1-haloalkadiene of the general formula (4) with a dihaloalkane of the general formula (5) to obtain the 1-haloalkadiene (1A) as shown below.

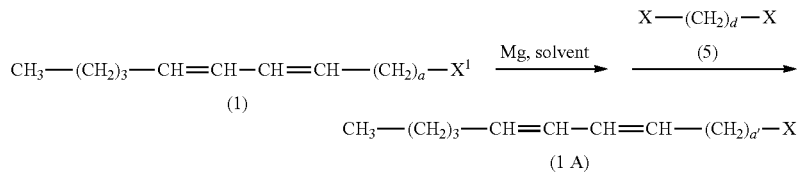

In the general formula (4), $X^1$ is a halogen atom as defined for X in the general formula (1), and c is an integer of 3 or from 5 to 12, preferably 3 or from 5 to 9, more preferably 3 or from 5 to 7. In general formula (5), X may be the same or different at each occurrence and is a halogen atom as defined for X in the general formula (1), d is an integer of from 3 to 12, preferably from 3 to 9, more preferably from 3 to 7, with a proviso 6<c+d<15. In the general formula (1A), a' is an integer of from 6 to 15, preferably from 6 to 13, more preferably from 6 to 8.

Illustrative geometrical isomers of the 1-haloalkadiene (4) include (E,E), (E,Z), (Z,E) and (Z,Z) isomers.

Examples of the 1-haloalkadiene (4) include a 1-halo-4,6-undecadiene (c=3), a 1-halo-6,8-tridecadiene (c=5), a 1-halo-7,9-tetradecadiene (c=6), a 1-halo-8,10-pentadecadiene (c=7), a 1-halo-9,11-hexadecadiene (c=8), a 1-halo-10,12-heptadecadiene (c=9), a 1-halo-11,13-octadecadiene (c=10), a 1-halo-12,14-nonadecadiene (c=11), and a 1-halo-13,15-eicosadiene (c=12).

Specific examples of the 1-halo-4,6-undecadiene include (4E,6E)-1-chloro-4,6-undecadiene, (4E,6Z)-1-chloro-4,6-undecadiene, (4Z,6E)-1-chloro-4,6-undecadiene, (4Z,6Z)-1-chloro-4,6-undecadiene, (4E,6E)-1-bromo-4,6-undecadiene, (4E,6Z)-1-bromo-4,6-undecadiene, (4Z,6E)-1-bromo-4,6-undecadiene, (4Z,6Z)-1-bromo-4,6-undecadiene, (4E,6E)-1-iodo-4,6-undecadiene, (4E,6Z)-1-iodo-4,6-undecadiene, (4Z,6E)-1-iodo-4,6-undecadiene, and (4Z,6Z)-1-iodo-4,6-undecadiene.

Specific examples of the 1-halo-6,8-tridecadiene include (6E,8E)-1-chloro-6,8-tridecadiene, (6E,8Z)-1-chloro-6,8-tridecadiene, (6Z,8E)-1-chloro-6,8-tridecadiene, (6Z,8Z)-1-chloro-6,8-tridecadiene, (6E,8E)-1-bromo-6,8-tridecadiene, (6E,8Z)-1-bromo-6,8-tridecadiene, (6Z,8E)-1-bromo-6,8-tridecadiene, (6Z,8Z)-1-bromo-6,8-tridecadiene, (6E,8E)-1-iodo-6,8-tridecadiene, (6E,8Z)-1-iodo-6,8-tridecadiene, (6Z,8E)-1-iodo-6,8-tridecadiene, and (6Z,8Z)-1-iodo-6,8-tridecadiene.

Specific examples of the 1-halo-7,9-tetradecadiene include (7E,9E)-1-chloro-7,9-tetradecadiene, (7E,9Z)-1-chloro-7,9-tetradecadiene, (7Z,9E)-1-chloro-7,9-tetradecadiene, (7Z,9Z)-1-chloro-7,9-tetradecadiene, (7E,9E)-1-bromo-7,9-tetradecadiene, (7E,9Z)-1-bromo-7,9-tetradecadiene, (7Z,9E)-1-bromo-7,9-tetradecadiene, (7Z,9Z)-1-bromo-7,9-tetradecadiene, (7E,9E)-1-iodo-7,9-tetradecadiene, (7E,9Z)-1-iodo-7,9-tetradecadiene, (7Z,9E)-1-iodo-7,9-tetradecadiene, and (7Z,9Z)-1-iodo-7,9-tetradecadiene.

Specific examples of the 1-halo-8,10-pentadecadiene include (8E,10Z)-1-chloro-8,10-pentadecadiene and (8E,10Z)-1-bromo-8,10-pentadecadiene.

Specific examples of the 1-halo-9,11-hexadecadiene include (9E,11Z)-1-chloro-9,11-hexadecadiene and (9E,11Z)-1-bromo-9,11-hexadecadiene.

Specific examples of the 1-halo-10,12-heptadecadiene include (10E,12Z)-1-chloro-10,12-heptadecadiene and (10E,12Z)-1-bromo-10,12-heptadecadiene.

Specific examples of the 1-halo-11,13-octadecadiene include (11E,13Z)-1-chloro-11,13-octadecadiene and (11E,13Z)-1-bromo-11,13-octadecadiene.

Specific examples of the 1-halo-12,14-nonadecadiene include (12E,14Z)-1-chloro-12,14-nonadecadiene and (12E,14Z)-1-bromo-12,14-nonadecadiene.

Specific examples of the 1-halo-13,15-eicosadiene include (13E,15Z)-1-chloro-13,15-eicosadiene and (13E,15Z)-1-bromo-13,15-eicosadiene.

Any of a commercially available or synthesized 1-haloalkadiene (4) may be used.

The alkadienyl magnesium halide may be prepared from a 1-haloalkadiene (4) by subjecting the 1-haloalkadiene (4) to a reaction with magnesium in a solvent.

The amount of magnesium to be used for the preparation of the alkadienyl magnesium halide from the 1-haloalkadiene (4) may range preferably from 1.0 to 2.0 gram atoms (24.3 to 48.6 g) per mol of the 1-haloalkadiene (4) for completion of the reaction.

Examples of the solvent to be used for the preparation of the alkadienyl magnesium halide from the 1-haloalkadiene (4) include ether solvents, such as tetrahydrofuran, diethyl ether and 4-methyltetrahydropyran; and hydrocarbon solvents, such as toluene, xylene and hexane. Tetrahydrofuran is preferred in view of the reaction rate of the Grignard reagent formation.

The amount of the solvent to be used may range preferably from 100 to 600 g per mol of the 1-haloalkadiene (4) in view of the reactivity.

The reaction temperature for the preparation of the alkadienyl magnesium halide from the 1-haloalkadiene (4) may vary, depending on the type of the solvent to be used. It ranges preferably from 30 to 120° C. in view of the reactivity.

The duration of the reaction for the preparation of the alkadienyl magnesium halide from the 1-haloalkadiene (4) may vary, depending on the type of the solvent or a scale of the reaction system. It ranges preferably from 1 to 30 hours in view of the reactivity.

In the general formula (5) for the dihaloalkane, X may be the same or different at each occurrence and is a halogen atom.

Illustrative combinations of X groups include chlorine and chlorine atoms, chlorine and bromine atoms, chlorine and iodine atoms, bromine and bromine atoms, bromine and iodine atoms, and iodine and iodine atoms.

Examples of the dihaloalkane (5) include a 1,3-dihalopropane (d=3), a 1,4-dihalobutane (d=4), a 1,5-dihalopentane (d=5), a 1,6-dihalohexane (d=6), a 1,7-dihaloheptane (d=7), a 1,8-dihalooctane (d=8), a 1,9-dihalononane (d=9), a 1,10-dihalodecane (d=10), a 1,11-dihaloundecane (d=11), and a 1,12-dihalododecane (d=12).

Specific examples of the 1,3-dihalopropane include 1,3-dichloropropane, 1-bromo-3-chloropropane, 1-chloro-3-iodopropane, 1,3-dibromopropane, 1-bromo-3-iodopropane, and 1,3-diiodopropane.

Specific examples of the 1,4-dihalobutane include 1,4-dichlorobutane, 1-bromo-4-chlorobutane, 1-chloro-4-iodobutane, 1,4-dibromobutane, 1-bromo-4-iodobutane, and 1,4-diiodobutane.

Specific examples of the 1,5-dihalopentane include 1,5-dichloropentane, 1-bromo-5-chloropentane, 1-chloro-5-iodopentane, 1,5-dibromopentane, 1-bromo-5-iodopentane, and 1,5-diiodopentane.

Specific examples of the 1,6-dihalohexane include 1,6-dichlorohexane, 1-bromo-6-chlorohexane, 1-chloro-6-iodohexane, 1,6-dibromohexane, 1-bromo-6-iodohexane, and 1,6-diiodohexane.

Specific examples of the 1,7-dihaloheptane include 1-bromo-7-chloroheptane, 1-chloro-7-iodoheptane, and 1-bromo-7-iodoheptane.

Specific examples of the 1,8-dihalooctane include 1-bromo-8-chlorooctane, 1-chloro-8-iodooctane, and 1-bromo-8-iodooctane.

Specific examples of the 1,9-dihalononane include 1-bromo-9-chlorononane, 1-chloro-9-iodononane, and 1-bromo-9-iodononane.

Specific examples of the 1,10-dihalodecane include 1-bromo-10-chlorodecane, 1-chloro-10-iododecane, and 1-bromo-10-iododecane.

Specific examples of the 1,11-dihaloundecane include 1-bromo-11-chloroundecane, 1-chloro-11-iodoundecane, and 1-bromo-11-iodoundecane.

Specific examples of the 1,12-dihalododecane include 1-bromo-12-chlorododecane, 1-chloro-12-iodododecane, and 1-bromo-12-iodododecane.

Any of a commercially available or synthesized dihaloalkane may be used.

The amount of the dihaloalkane (5) to be used may range preferably from 1.0 to 10.0 mol, more preferably from 1.0 to 3.0 mol, per mol of the 1-haloalkadiene (4), in view of the reactivity.

In a case where two different X groups are used, the coupling reaction may be conducted so that the reaction with X group of a higher reactivity proceeds preferentially by appropriately selecting the catalyst and the reaction temperature as described later. For example, when the combination of chlorine and bromine atoms or of chlorine and iodine atoms is used as the different X groups in the dihaloalkane (5), a product having a chlorine atom as the X group in the general formula (1A) can be obtained. When the combination of bromine and iodine atoms is used as the different X groups in the dihaloalkane (5), a product having a bromine atom as the X group in the general formula (1A) can be obtained.

A catalyst may be used for the coupling reaction, if necessary in view of the reactivity.

Examples of the catalyst for the coupling reaction include copper (I) halides, such as cuprous chloride, cuprous bromide and cuprous iodide; copper (I) compounds, such as cuprous cyanide and cuprous oxide; copper (II) halides, such as cupric chloride, cupric bromide and cupric iodide; and copper (II) compounds, such as cupric cyanide, cupric oxide, and dilithium tetrachlorocuprate. Copper halides such as cuprous iodide are preferred in view of the reactivity.

For an economical reason, the amount of the catalyst to be used may range preferably from 0.003 to 0.300 mol, more preferably 0.003 to 0.030 mol, per mol of the 1-haloalkadiene (4).

In the coupling reaction, the catalyst is preferably used in combination with a cocatalyst.

Examples of the cocatalyst include phosphorus compounds, in particular trialkyl phosphites having 3 to 9 carbon atoms, such as triethyl phosphite; and triarylphosphines having 18 to 21 carbon atoms, such as triphenylphosphine. In view of the reactivity, triethyl phosphite is preferred.

The amount of the cocatalyst to be used may range preferably from 0.001 to 0.500 mol, more preferably 0.001 to 0.050 mol, per mol of the 1-haloalkadiene (4).

Examples of the solvent to be used in the coupling reaction include ether solvents, such as tetrahydrofuran, diethyl ether and 4-methyltetrahydropyran; and hydrocarbon solvents, such as toluene, xylene and hexane. Tetrahydrofuran is preferred in view of the reactivity.

The amount of the solvent to be used may range preferably from 50 to 800 g per mol of the 1-haloalkadiene (4) in view of the reactivity.

The temperature for the coupling reaction may range preferably from 0 to 30° C. in view of the reactivity.

The duration of the coupling reaction may vary, depending on a scale of the reaction system. It ranges preferably from 0.1 to 20 hours in view of the reactivity.

In one embodiment of the process for preparing a 1-haloalkadiene (1A), a (8E,10Z)-1-halo-8,10-pentadecadiene of the following general formula (1-3) may be prepared by a coupling reaction of a (4E,6Z)-4,6-undecadienyl magnesium halide derived from a (4E,6Z)-1-halo-4,6-undecadiene of the following general formula (4-1) with a 1,4-dihalobutane of the following general formula (5-2).

In the process of preparing (9E,11Z)-9,11-hexadecadienyl acetate, the step of conducting a Wittig reaction between a (2E)-9-halo-2-nonenal of the general formula (2-1) and a triarylphosphonium pentylide of the general formula (3) to obtain a (7E,9Z)-1-halo-7,9-tetradecadiene of the general formula (1-1) may be carried out as will be described below.

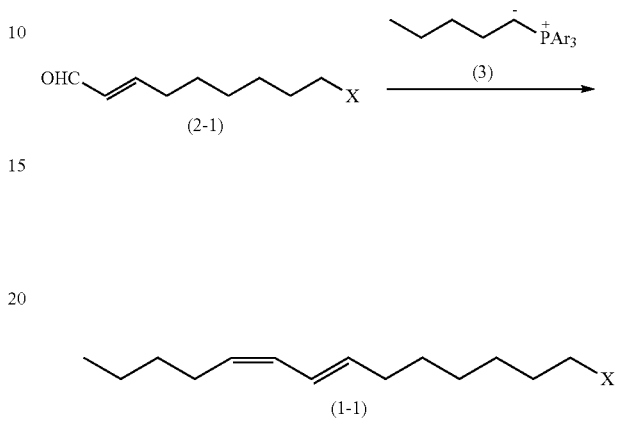

The (2E)-9-halo-2-nonenal (2-1) and triarylphosphonium pentylide (3) used in the Wittig reaction are as already described above, and the Wittig reaction may be carried out under the conditions as already described above.

Specific examples of the (7E,9Z)-1-halo-7,9-tetradecadiene (1-1) are already mentioned above in connection with the 1-halo-7,9-tetradecadienes among the 1-haloalkadienes (1).

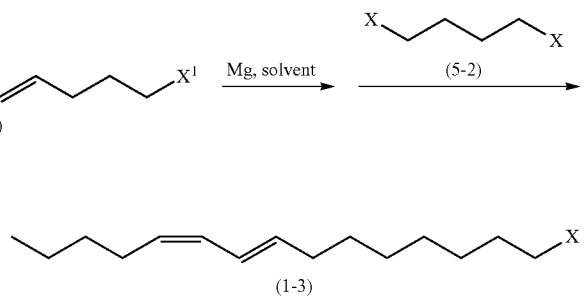

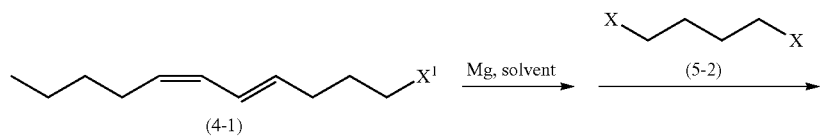

In another embodiment of the process for preparing a 1-haloalkadiene (1A), a (13E,15Z)-1-halo-13,15-eicosadiene of the following general formula (1-4) may be prepared by a coupling reaction of a (7E,9Z)-7,9-tetradecadienyl magnesium halide derived from a (7E,9Z)-1-halo-7,9-tetradecadiene of the following general formula (4-2) with a 1,6-dihalohexane of the following general formula (5-3).

In the process of preparing (9E,11Z)-9,11-hexadecadienyl acetate, the step of subjecting a (7E,9Z)-7,9-tetradecadienyl magnesium halide derived from a (7E,9Z)-1-halo-7,9-tetradecadiene of the general formula (1-1) to an addition reaction with ethylene oxide to obtain (9E,11Z)-9,11-hexadecadienol of the formula (6) may be carried out as will be described below.

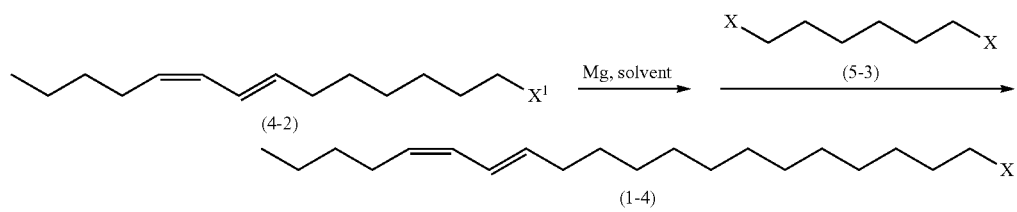

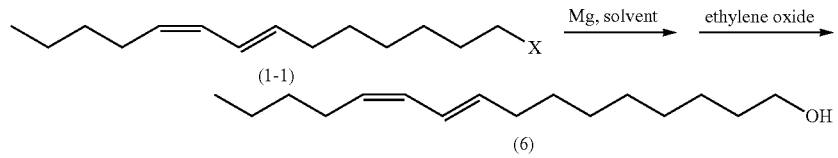

In the general formula (1-1) for the (7E,9Z)-1-halo-7,9-tetradecadiene, X is as defined above for X in the general formula (1).

Specific examples of the (7E,9Z)-1-halo-7,9-tetradecadiene (1-1) include (7E,9Z)-1-chloro-7,9-tetradecadiene, (7E,9Z)-1-bromo-7,9-tetradecadiene, and (7E,9Z)-1-iodo-7,9-tetradecadiene.

The (7E,9Z)-7,9-tetradecadienyl magnesium halide may be prepared from a (7E,9Z)-1-halo-7,9-tetradecadiene (1-1) by subjecting the (7E,9Z)-1-halo-7,9-tetradecadiene (1-1) to a reaction with magnesium in a solvent.

The amount of magnesium to be used for the preparation of the (7E,9Z)-7,9-tetradecadienyl magnesium halide from the (7E,9Z)-1-halo-7,9-tetradecadiene (1-1) may range preferably from 1.0 to 2.0 gram atoms (24.3 to 48.6 g) per mol of the (7E,9Z)-1-halo-7,9-tetradecadiene (1-1) for completion of the reaction.

Examples of the solvent to be used for the preparation of the (7E,9Z)-7,9-tetradecadienyl magnesium halide from the (7E,9Z)-1-halo-7,9-tetradecadiene (1-1) include ether solvents, such as tetrahydrofuran, diethyl ether and 4-methyltetrahydropyran; and hydrocarbon solvents, such as toluene, xylene and hexane. Tetrahydrofuran is preferred in view of the reaction rate of the Grignard reagent formation.

The amount of the solvent to be used may range preferably from 100 to 600 g per mol of the (7E,9Z)-1-halo-7,9-tetradecadiene (1-1) in view of the reactivity.

The reaction temperature for the preparation of the (7E,9Z)-7,9-tetradecadienyl magnesium halide from the (7E,9Z)-1-halo-7,9-tetradecadiene (1-1) may vary, depending on the type of the solvent to be used. It ranges preferably from 30 to 120° C. in view of the reactivity.

The duration of the reaction for the preparation of the (7E,9Z)-7,9-tetradecadienyl magnesium halide from the (7E,9Z)-1-halo-7,9-tetradecadiene (1-1) may vary, depending on the type of the solvent and a scale of the reaction system. It ranges preferably from 1 to 30 hours in view of the reactivity.

Examples of the (7E,9Z)-7,9-tetradecadienyl magnesium halide derived from (7E,9Z)-1-halo-7,9-tetradecadiene (1-1) include (7E,9Z)-7,9-tetradecadienyl magnesium chloride, (7E,9Z)-7,9-tetradecadienyl magnesium bromide, and (7E,9Z)-7,9-tetradecadienyl magnesium iodide.

The amount of ethylene oxide to be used may range preferably from 1.0 to 5.0 mol, more preferably 1.0 to 2.0 mol, per mol of the (7E,9Z)-1-halo-7,9-tetradecadiene (1-1), in view of the reactivity.

A catalyst may be used for the addition reaction with ethylene oxide, if necessary in view of the reactivity.

Examples of the catalyst that may be used in the addition reaction with ethylene oxide include copper (I) halides, such as cuprous chloride, cuprous bromide and cuprous iodide; copper (I) compounds, such as cuprous cyanide and cuprous oxide; copper (II) halides, such as cupric chloride, cupric bromide and cupric iodide; and copper (II) compounds, such as cupric cyanide, cupric oxide, and dilithium tetrachlorocuprate. Copper halides such as cuprous iodide are preferred in view of the reactivity.

For the economical reasons, the amount of the catalyst to be used in the addition reaction with ethylene oxide may range preferably from 0.0001 to 0.1000 mol, more preferably from 0.001 to 0.010 mol, per mol of the (7E,9Z)-1-halo-7,9-tetradecadiene (1-1).

The type and amount of the solvent used in the addition reaction with ethylene oxide may be the same as or different from those used for the preparation of the (7E,9Z)-7,9-tetradecadienyl magnesium from the (7E,9Z)-1-halo-7,9-tetradecadiene (1-1).

The optimum temperature for the addition reaction with ethylene oxide may vary, depending on the type of the solvent to be used. It ranges preferably from −78 to 40° C., more preferably −10 to 30° C.

The duration of the addition reaction with ethylene oxide may vary, depending on a scale of the reaction system. It ranges preferably from 0.1 to 20 hours.

In the process of preparing (9E,11Z)-9,11-hexadecadienyl acetate, the step of conducting an acetylation reaction of (9E,11Z)-9,11-hexadecadienol of the general formula (6) with an acylating agent to obtain (9E,11Z)-9,11-hexadecadienyl acetate may be carried out as will be described below.

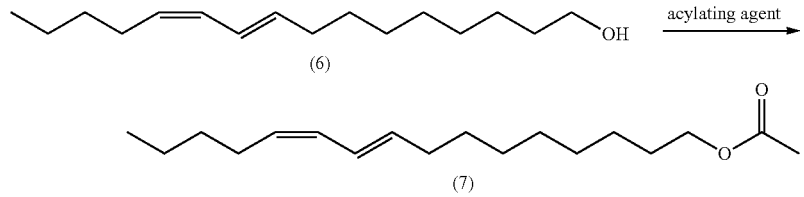

Examples of the acylating agent include acetic anhydride, acetic acid, acetyl halides such as acetyl chloride, and acetate esters, such as methyl acetate and ethyl acetate.

The amount of the acylating agent may range preferably from 1.0 to 10.0 mol, more preferably from 1.0 to 5.0 mol, per mol of (9E,11Z)-9,11-hexadecadienol (6), in view of the reactivity and for the economical reasons.

If necessary, an acid or base may be used in the acetylation reaction.

Examples of the acid include mineral acids, aromatic sulfonic acids and Lewis acids. Examples of the mineral acid include hydrochloric acid and sulfuric acid. Examples of the aromatic sulfonic acid include benzenesulfonic acid and p-toluenesulfonic acid. Examples of the Lewis acid include boron trifluoride etherate and tetraisopropyl orthotitanate. These acids may be used alone or in combination.

The amount of the acid to be used may range preferably from 0.01 to 1.00 mol, more preferably from 0.01 to 0.50 mol, per mol of (9E,11Z)-9,11-hexadecadienol (6), in view of the reactivity and for the economical reasons.

Examples of the base include amines and metal alkoxides.

Examples of the amines include trialkylamines, such as trimethylamine, triethylamine and N,N-diisopropylethylamine; and aromatic amine compounds, such as pyridine, dimethylaniline and 4-dimethylaminopyridine. Examples of the metal alkoxides include potassium t-butoxide and sodium methoxide. These bases may be used alone or in combination.

The amount of the base to be used may range preferably from 1.0 to 10.0 mol, more preferably from 1.0 to 3.0 mol, per mol of (9E,11Z)-9,11-hexadecadienol (6), in view of the reactivity and for the economical reasons.

Examples of the solvent to be used for acetylation reaction include halogenic solvents, such as dichloromethane and chloroform; ether solvents, such as tetrahydrofuran, diethyl ether and 4-methyltetrahydropyran; and hydrocarbon solvents, such as toluene, xylene and hexane. The halogenic and ether solvents are preferred in view of the reactivity. It should be noted that the reaction may be carried out in a solvent-free fashion, depending on the type of catalyst to be used. These solvents may be used alone or in combination.

The amount of the solvent to be used may range preferably from 0 to 3,000 g per mol of (9E,11Z)-9,11-hexadecadienol (6) in view of the reactivity.

The temperature during the acetylation reaction may vary, depending on the type of the solvent to be used. It ranges preferably from 0 to 100° C., more preferably from 25 to 80° C., in view of the reactivity and yield.

The duration of the acetylation reaction may vary, depending on the type of the solvent or a scale of the reaction system. It ranges preferably from 1 to 30 hours in view of the reactivity.

In the process of preparing (9E,11Z)-9,11-hexadecadienyl acetate, the step of conducting a coupling reaction of a (4E,6Z)-4,6-undecadienyl magnesium halide derived from a (4E,6Z)-1-halo-4,6-undecadiene of the general formula (4-1) with a 1,5-dihalopentane of the general formula (5-1) to obtain a (9E,11Z)-1-halo-9,11-hexadecadiene of the general formula (1-2) may be carried out as will be described below.

Examples of the (4E,6Z)-4,6-undecadienyl magnesium halide derived from a (4E,6Z)-1-halo-4,6-undecadiene include (4E,6Z)-4,6-undecadienyl magnesium chloride, (4E,6Z)-4,6-undecadienyl magnesium bromide, and (4E,6Z)-4,6-undecadienyl magnesium iodide.

The 1,5-dihalopentanes (5-1) that may be used in the coupling reaction are as already described above, and the coupling reaction may be carried out under the conditions as already described above.

Specific examples of the (4E,6Z)-1-halo-4,6-undecadiene (4-1) and of the (9E,11Z)-1-halo-9,11-hexadecadiene (1-2) are already mentioned above in connection with the 1-halo-4,6-undecadienes and the 1-halo-9,11-hexadecadienes among the 1-haloalkadienes (1), respectively.

In the process of preparing (9E,11Z)-9,11-hexadecadienyl acetate, the step of substituting the halogen atom of the (9E,11Z)-1-halo-9,11-hexadecadiene of the general formula (1-2) with an acetoxy group to obtain (9E,11Z)-9,11-hexadecadienyl acetate of the general formula (7) may be carried out as will be described below.

Illustrative processes for substituting the halogen atom of the (9E,11Z)-1-halo-9,11-hexadecadiene (1-2) with an acetoxy group include a process of subjecting the (9E,11Z)-1-halo-9,11-hexadecadiene (1-2) to an acetoxylation reaction with an acetate salt; a process of reacting the (9E,11Z)-1-halo-9,11-hexadecadiene (1-2) with an alkali metal hydroxide to form (9E,11Z)-9,11-hexadecadienol (6), followed by acetylation thereof and a process of reacting the (9E,11Z)-1-halo-9,11-hexadecadiene (1-2) with a metal alkoxide, and subsequent cleavage of the resulting ether by a strong acid to form (9E,11Z)-9,11-hexadecadienol (6), followed by acetylation thereof. In view of the number of steps, the process of subjecting the (9E,11Z)-1-halo-9,11-hexadecadiene (1-2) to an acetoxylation reaction with an acetate salt of the general formula (8) may be preferred.

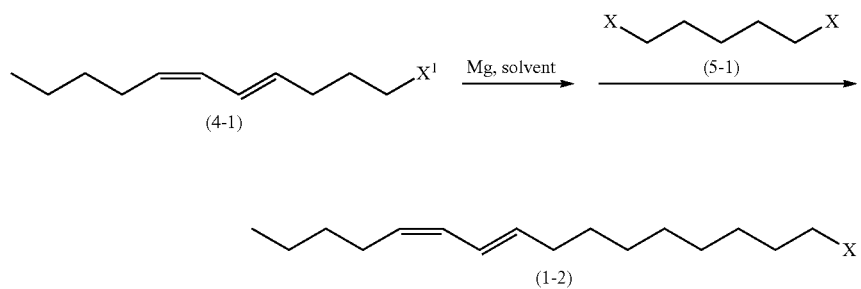

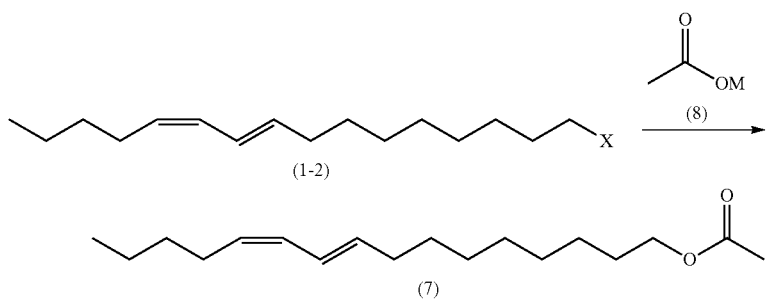

In the general formula (8), M is a metal atom, examples of which preferably include alkali metals, such as lithium, sodium and potassium.

In the general formula (1-2) for the (9E,11Z)-1-halo-9, 11-hexadecadienes, X is as defined for X in the general formula (1).

Specific examples of the (9E,11Z)-1-halo-9,11-hexadecadiene (1-2) include (9E,11Z)-1-chloro-9,11-hexadecadiene, (9E,11Z)-1-bromo-9,11-hexadecadiene, and (9E,11Z)-1-iodo-9,11-hexadecadiene.

Specific examples of the acetate salt (8) include lithium acetate, sodium acetate and potassium acetate. Sodium acetate is preferred in view of the reactivity.

The amount of the acetate salt (8) to be used may range preferably from 1.0 to 5.0 mol per mol of the (9E,11Z)-1-halo-9,11-hexadecadiene (1-2) in view of the reactivity.

If necessary, another salt may also be added in the acetoxylation reaction for promoting the reaction.

Examples of the salt include iodide salts and silver salts.

Examples of the iodide salt include alkali metal iodides, such as lithium iodide, sodium iodide and potassium iodide; alkaline earth meal iodides, such as magnesium iodide and calcium iodide; tetraalkylammonium iodides, such as tetrabutylammonium iodide; tetraalkyl phosphonium iodides, such as tetrabutylphosphonium iodide; and ammonium iodide.

Examples of the silver salt include silver (I) halides, such as silver (I) chloride, silver (I) bromide, and silver (I) iodide; and silver nitrate.

The amount of the salt to be added may range preferably from 0.0001 to 5.0000 mol per mol of the (9E,11Z)-1-halo-9,11-hexadecadiene (1-2) in view of the reactivity and for the economical reasons.

Examples of the solvent that may be used in the acetoxylation include aprotic non-polar solvents, such as N,N-dimethylformamide, N,N-dimethylacetamide, N,N-dimethylpropionamide, 1,3-dimethyl-2-imidazolidinone, dimethyl sulfoxide and hexamethylphosphoric triamide; ether solvents, such as tetrahydrofuran, diethyl ether and 4-methyltetrahydropyran; and hydrocarbon solvents, such as toluene, xylene and hexane. N,N-Dimethylacetamide is preferred in view of the reaction rate.

The amount of the solvent to be used may range preferably from 1 to 300 g per mol of the (9E,11Z)-1-halo-9,11-hexadecadiene (1-2) in view of the reactivity.

The temperature during the acetoxylation may vary, depending on the type of the solvent to be used. It ranges preferably from 0 to 150° C., more preferably from 20 to 125° C., in view of the reactivity.

The duration of the acetoxylation may vary, depending on the type of the solvent or a scale of the reaction system. It ranges preferably from 1 to 50 hours in view of the reactivity.

It is also possible to prepare (9E,11Z)-9,11-hexadecadienyl acetate (7) by reacting a (9E,11Z)-1-halo-9,11-hexadecadiene with an alkali metal hydroxide to form (9E,11Z)-9,11-hexadecadienol, followed by acetylation thereof.

Examples of the alkali metal hydroxide include lithium hydroxide, sodium hydroxide, and potassium hydroxide.

The acetylation may be carried out in a conventional way.

It is also possible to prepare (9E,11Z)-9,11-hexadecadienyl acetate (7) by reacting a (9E,11Z)-1-halo-9,11-hexadecadiene (1-2) with a metal alkoxide, and subsequent cleavage of the resulting ether by a strong acid to form (9E,11Z)-9,11-hexadecadienol, followed by acetylation thereof.

Examples of the metal alkoxide include sodium t-butoxide and potassium t-butoxide.

The ether cleavage by a strong acid and the acetylation may be carried out each in a conventional way.

As described above, a 1-haloalkadiene useful as an intermediate and a process of its production and an efficient process for preparing (9E,11Z)-9,11-hexadecadienyl acetate (7), sex pheromone of the pecan nut casebearer (*Acrobasis nuxvorella*), are now provided.

EXAMPLES

The invention will be further described with reference to the following Examples.

It should be construed that the invention is not limited to or by the Examples.

Example 1

Preparation of (7E,9Z)-1-chloro-7,9-tetradecadiene (1-1: X=Cl)

To a reactor were charged 1-bromopentane (185 g, 1.20 mol), triphenylphosphine (321 g, 1.20 mol) and N,N-dimethylformamide (225 g), and the resulting mixture was stirred at 110 to 115° C. for 6 hours to prepare pentyltriphenylphosphonium bromide. The reaction mixture was cooled to 20 to 30° C., to which was added tetrahydrofuran (967 g). Then, it was cooled to 0 to 10° C., to which was added potassium t-butoxide (139 g, 1.20 mol). It was stirred at 10 to 15° C. for 30 minutes, and then (2E)-9-chloro-2-nonenal (2-1: X=Cl) (171 g, 0.978 mol) was added dropwise at −5 to 5° C. After completion of the dropwise addition, the reaction mixture was stirred for 3 hours, and then the reaction was stopped by the addition of water (593 g) to the reaction mixture. After removal of the aqueous layer by liquid-liquid separation, the organic layer was concentrated by evaporating the solvent under vacuum. Then, hexane (713 g) was added to cause precipitation of triphenylphosphineoxide, which was then removed by filtration. The filtrate was concentrated by evaporating the solvent under vacuum, and the resulting concentrate was subjected to distillation under vacuum to obtain (7E,9Z)-1-chloro-7,9-tetradecadiene (1-1: X=Cl) (204 g, 0.892 mol) with a yield of 94.1%.

Characterization of
(7E,9Z)-1-chloro-7,9-tetradecadiene (1-1: X=Cl)

[NMR Spectra] $^1$H-NMR (500 MHz, CDCl$_3$): δ0.91 (3H, t, J=7.3 Hz), 1.31-1.47 (10H, m), 1.77 (2H, tt, J=6.9, 6.9 Hz), 2.10 (2H, dt, J=7.7, 7.7 Hz), 2.16 (2H, dt, J=6.9, 6.9 Hz), 3.53 (2H, t, J=6.9 Hz), 5.31 (1H, dt, J=10.7, 7.7 Hz), 5.64 (1H, dt, J=15.3, 6.9 Hz), 5.94 (1H, dd, J=10.7, 10.7 Hz), 6.30 (1H, dd, J=15.3, 10.7 Hz); $^{13}$C-NMR (75.6 MHz, CDCl$_3$): 13.94, 22.30, 26.69, 27.37, 28.39, 29.17, 31.87, 32.55, 32.68, 44.08, 125.81, 128.48, 130.21, 134.19.

[Mass Spectrum] EI-Mass Spectrum (70 eV): m/z 228 (M+), 157, 144, 123, 109, 95, 81, 67, 54, 41, 27.

[IR Absorption Spectrum] (NaCl): vmax 3018, 2956, 2928, 2856, 1464, 1377, 1309, 983, 949, 728, 653.

Example 2

Preparation of
(8E,10Z)-1-chloro-8,10-pentadecadiene (1-3: X=Cl)

To a reactor were charged magnesium (17.8 g, 0.733 gram atom) and tetrahydrofuran (198 g), and the resulting mixture was stirred at 60 to 65° C. for 30 minutes. Then, (4E,6Z)-1-chloro-4,6-undecadiene (4-1: X$^1$=Cl) (124 g, 0.667 mol) was added dropwise at 60 to 70° C., and the resulting mixture was stirred at 70 to 75° C. for 6 hours to prepare (4E,6Z)-4,6-undecadienyl magnesium chloride. To another reactor were charged cuprous iodide (1.27 g, 0.00667 mol), triethyl phosphite (2.66 g, 0.0160 mol), 1-bromo-4-chlorobutane (131 g, 0.767 mol) and tetrahydrofuran (66.1 g), and the resulting mixture was stirred at 0 to 5° C. for 30 minutes. Then, the solution of (4E,6Z)-4,6-undecadienyl magnesium chloride in tetrahydrofuran as prepared above was added dropwise at 5 to 15° C. After completion of the dropwise addition, the reaction mixture was stirred at 5 to 10° C. for 2 hours, and then the reaction was stopped by the addition of ammonium chloride (6.29 g), 20 wt % aqueous hydrogen chloride (10.1 g) and water (176 g) to the reaction mixture. After removal of the aqueous layer by liquid-liquid separation, the organic layer was concentrated by evaporating the solvent under vacuum, and the resulting concentrate was subjected to distillation under vacuum to obtain (8E, 10Z)-1-chloro-8,10-pentadecadiene (1-3: X=Cl) (145 g, 0.596 mol) with a yield of 89.3%.

Characterization of
(8E,10Z)-1-chloro-8,10-pentadecadiene (1-3: X=Cl)

[NMR Spectra] $^1$H-NMR (500 MHz, CDCl$_3$): δ0.91 (3H, t, J=6.9 Hz), 1.29-1.46 (12H, m), 1.77 (2H, tt, J=6.9, 6.9 Hz), 2.10 (2H, dt, J=6.9, 6.9 Hz), 2.16 (2H, dt, J=6.9, 6.9 Hz), 3.53 (2H, t, J=6.9 Hz), 5.31 (1H, dt, J=10.7, 7.7 Hz), 5.64 (1H, dt, J=15.3, 6.9 Hz), 5.94 (1H, dd, J=10.7, 10.7 Hz), 6.30 (1H, dd, J=15.3, 10.7 Hz); $^{13}$C-NMR (75.6 MHz, CDCl$_3$): 13.94, 22.30, 26.80, 27.37, 28.72, 28.98, 29.25, 31.88, 32.59, 32.78, 45.10, 125.71, 128.52, 130.13, 134.38.

[Mass Spectrum] EI-Mass Spectrum (70 eV): m/z 242 (M+), 158, 144, 123, 109, 95, 81, 67, 55, 41, 27.

[IR Absorption Spectrum] (NaCl): vmax 3018, 2955, 2928, 2856, 1465, 1377, 1309, 982, 948, 727, 654.

Example 3

Preparation of
(9E,11Z)-1-chloro-9,11-hexadecadiene (1-2: X=Cl)

To a reactor were charged magnesium (13.1 g, 0.540 gram atom) and tetrahydrofuran (146 g), and the resulting mixture was stirred at 60 to 65° C. for 30 minutes. Then, (4E,6Z)-1-chloro-4,6-undecadiene (4-1: X$^1$=Cl) (91.7 g, 0.491 mol) was added dropwise at 60 to 70° C., and then the resulting mixture was stirred at 70 to 75° C. for 6 hours to prepare (4E,6Z)-4,6-undecadienyl magnesium chloride. To another reactor were charged cuprous iodide (0.98 g, 0.0049 mol), triethyl phosphite (1.96 g, 0.0118 mol), 1-bromo-5-chloropentane (105 g, 0.565 mol) and tetrahydrofuran (48.7 g), and the resulting mixture was stirred at 0 to 5° C. for 30 minutes. Then, the solution of (4E,6Z)-4,6-undecadienyl magnesium chloride in tetrahydrofuran as prepared above was added dropwise at 5 to 15° C. After completion of the dropwise addition, the resulting reaction mixture was stirred at 5 to 10° C. for 3 hours, and then the reaction was stopped by the addition of ammonium chloride (4.63 g), 20 wt % aqueous hydrogen chloride (7.46 g) and water (130 g) to the reaction mixture. After removal of the aqueous layer by liquid-liquid separation, the organic layer was concentrated by evaporating the solvent under vacuum, and the resulting concentrate was subjected to distillation under vacuum to obtain (9E, 11Z)-1-chloro-9,11-hexadecadiene (1-2: X=Cl) (106 g, 0.412 mol) with a yield of 84.1%.

Characterization of
(9E,11Z)-1-chloro-9,11-hexadecadiene (1-2: X=Cl)

[NMR Spectra] $^1$H-NMR (500 MHz, CDCl$_3$): δ0.91 (3H, t, J=6.9 Hz), 1.31-1.44 (14H, m), 1.77 (2H, tt, J=6.9, 6.9 Hz), 2.09 (2H, dt, J=6.9, 6.9 Hz), 2.16 (2H, dt, J=6.9, 6.9 Hz), 3.53 (2H, t, J=6.9 Hz), 5.30 (1H, dt, J=11.1, 7.3 Hz), 5.65 (1H, dt, J=14.9, 6.9 Hz), 5.94 (1H, dd, J=11.1, 11.1 Hz), 6.30 (1H, dd, J=14.9, 11.1 Hz); $^{13}$C-NMR (75.6 MHz, CDCl$_3$): 13.95, 22.31, 26.86, 27.38, 28.82, 29.08, 29.29, 29.34, 31.89, 32.62, 32.82, 45.12, 125.66, 128.55, 130.08, 134.50.

[Mass Spectrum] EI-Mass Spectrum (70 eV): m/z 256 (M+), 172, 158, 144, 124, 110, 95, 81, 67, 41, 27.

[IR Absorption Spectrum] (NaCl): vmax 3018, 2955, 2927, 2855, 1465, 1377, 1309, 983, 948, 726, 654.

Example 4

Preparation of
(13E,15Z)-1-chloro-13,15-eicosadiene (1-4: X=Cl)

To a reactor were charged magnesium (5.53 g, 0.228 gram atom) and tetrahydrofuran (61.5 g), and the resulting mixture was stirred at 60 to 65° C. for 30 minutes. Then, (7E,9Z)-1-chloro-7,9-tetradecadiene (4-2: X$^1$=Cl) (47.4 g, 0.207 mol) was added dropwise at 60 to 70° C., and the resulting mixture was stirred at 70 to 75° C. for 4 hours to prepare (7E,9Z)-7,9-tetradecadienyl magnesium chloride. To another reactor were charged cuprous iodide (0.42 g, 0.0021 mol), triethyl phosphite (0.83 g, 0.0050 mol), 1-bromo-6-chlorohexane (50.0 g, 0.238 mol) and tetrahydrofuran (20.5 g), and the resulting mixture was stirred at 0 to 5° C. for 30 minutes. Then, the solution of (7E,9Z)-7,9-tetradecadienyl magnesium chloride in tetrahydrofuran as prepared above was added dropwise at 5 to 15° C. After completion of the dropwise addition, the reaction mixture was stirred at 5 to 10° C. for 1 hour, and then the reaction was stopped by the addition of ammonium chloride (1.95 g), 20 wt % aqueous hydrogen chloride (3.14 g) and (54.8 g) to the reaction mixture. After removal of the aqueous layer by liquid-liquid separation, the organic layer was concentrated by evaporating the solvent under vacuum, and the resulting concentrate was subjected to distillation under vacuum to obtain (13E,15Z)-1-chloro-13,15-eicosadiene (1-4: X=Cl) (53.3 g, 0.170 mol) with a yield of 82.2%.

Characterization of
(13E,15Z)-1-chloro-13,15-eicosadiene (1-4: X=Cl)

[NMR Spectra] $^1$H-NMR (500 MHz, CDCl$_3$): δ0.91 (3H, t, J=6.9 Hz), 1.26-1.45 (22H, m), 1.77 (2H, tt, J=6.5, 6.5 Hz), 2.09 (2H, dt, J=7.6, 7.6 Hz), 2.16 (2H, dt, J=7.3, 7.3 Hz), 3.53 (2H, t, J=6.5 Hz), 5.30 (1H, dt, J=10.7, 7.6 Hz), 5.65 (1H, dt, J=14.9, 7.3 Hz), 5.94 (1H, dd, J=10.7, 10.7 Hz), 6.30 (1H, dd, J=14.9, 10.7 Hz); $^{13}$C-NMR (75.6 MHz, CDCl$_3$): 13.95, 22.31, 26.88, 27.38, 28.89, 29.22, 29.40, 29.45, 29.49, 29.53, 29.58 (2C), 31.90, 32.64, 32.88, 45.15, 125.59, 128.59, 130.01, 134.64.
[Mass Spectrum] EI-Mass Spectrum (70 eV): m/z 312 (M$^+$), 124, 109, 96, 81, 67, 55, 43, 27.
[IR Absorption Spectrum] (NaCl): νmax 3018, 2925, 2854, 1465, 1377, 1308, 983, 948, 726, 654.

Example 5

Preparation of (9E,11Z)-9,11-hexadecadienol (6)

To a reactor were charged magnesium (4.95 g, 0.204 gram atom) and tetrahydrofuran (19.4 g), and the resulting mixture was stirred at 60 to 65° C. for 30 minutes. Then, (7E,9Z)-1-chloro-7,9-tetradecadiene (1-1: X$^1$=Cl) (42.4 g, 0.185 mol) was added dropwise at 60 to 70° C., and the resulting mixture was stirred at 70 to 75° C. for 3 hours to prepare (7E,9Z)-7,9-tetradecadienyl magnesium chloride. Then, it was stirred at 0 to 5° C. for 30 minutes, and cuprous chloride (0.04 g, 0.0004 mol) was added, followed by the dropwise addition of ethylene oxide (10.2 g, 0.232 mol). The resulting mixture was stirred at 20 to 25° C. for 1 hour, and then acetic acid (18.4 g) and water (118 g) were added dropwise at 20 to 30° C. After removal of the aqueous layer by liquid-liquid separation of the resulting reaction mixture, the organic layer was concentrated by evaporating the solvent under vacuum, and the resulting concentrate was subjected to distillation under vacuum to obtain (9E,11Z)-9,11-hexadecadienol (6) (38.4 g, 0.161 mol) with a yield of 87.0%.

Characterization of (9E,11Z)-9,11-hexadecadienol (6)

[NMR Spectra] $^1$H-NMR (500 MHz, CDCl$_3$): δ0.90 (3H, t, J=6.9 Hz), 1.29-1.39 (14H, m), 1.49 (1H, brs), 1.56 (2H, tt, J=6.9, 6.9 Hz), 2.08 (2H, dt, J=6.9, 6.9 Hz), 2.16 (2H, dt, J=6.9, 6.9 Hz), 3.62 (2H, t, J=6.9 Hz), 5.29 (1H, dt, J=10.7, 6.9 Hz), 5.64 (1H, dt, J=15.3, 6.9 Hz), 5.93 (1H, dd, J=10.7, 10.7 Hz), 6.29 (1H, dd, J=15.3, 10.7 Hz); $^{13}$C-NMR (75.6 MHz, CDCl$_3$): 13.93, 22.28, 25.68, 27.35, 29.11, 29.35 (2C), 29.41, 31.86, 32.73, 32.82, 62.99, 125.60, 128.55, 130.04, 134.55.
[Mass Spectrum] EI-Mass Spectrum (70 eV): m/z 238 (M$^+$), 121, 109, 95, 81, 67, 55, 41, 29.
[IR Absorption Spectrum] (NaCl): νmax 3463, 3037, 2918, 2863, 1606, 1505, 1453, 1298, 1220, 1176, 1004, 822, 733, 593.

Example 6

Preparation of (9E,11Z)-9,11-hexadecadienyl acetate (7)

To a reactor were charged (9E,11Z)-9,11-hexadecadienol (6) (67.2 g, 0.282 mol) and pyridine (35.7 g, 0.451 mol), and the resulting mixture was stirred at 30 to 35° C. for 30 minutes. Then, acetic anhydride (14.2 g, 0.139 mol) was added dropwise, and the resulting mixture was stirred at 35 to 40° C. for 1 hour. Then, after the addition of water (75.8 g), the resulting reaction mixture was allowed to separate into two layers, and the organic layer was washed with a solution of sodium chloride (2.28 g) and water (28.5 g). It was concentrated by evaporating the solvent under vacuum, and the resulting concentrate was subjected to distillation under vacuum to obtain (9E,11Z)-9,11-hexadecadienyl acetate (7) (59.3 g, 0.211 mol) with a yield of 76.0%.

Characterization of (9E,11Z)-9,11-hexadecadienyl acetate (7)

[NMR Spectra] $^1$H-NMR (500 MHz, CDCl$_3$): δ0.90 (3H, t, J=6.9 Hz), 1.29-1.40 (14H, m), 1.61 (2H, tt, J=6.9, 6.9 Hz), 2.04 (3H, s), 2.08 (2H, dt, J=6.9, 6.9 Hz), 2.31 (2H, dt, J=6.9, 6.9 Hz), 4.04 (2H, t, J=6.9 Hz), 5.29 (1H, dt, J=11.1, 6.9 Hz), 5.64 (1H, dt, J=15.3, 6.9 Hz), 5.93 (1H, dd, J=11.1, 11.1 Hz), 6.29 (1H, dd, J=15.3, 11.1 Hz); $^{13}$C-NMR (75.6 MHz, CDCl$_3$): 13.93, 20.97, 22.29, 25.86, 27.35, 28.55, 29.09, 29.17, 29.33 (2C), 31.87, 32.82, 64.59, 125.63, 128.55, 130.05, 134.50, 171.18.
[Mass Spectrum] EI-Mass Spectrum (70 eV): m/z 280 (M$^+$), 220, 192, 177, 163, 149, 135, 121, 95, 81, 67, 43, 29.
[IR Absorption Spectrum] (NaCl): νmax 3019, 2927, 2855, 1742, 1465, 1365, 1239, 1039, 982, 949, 725, 606.

Example 7

Preparation of (9E,11Z)-9,11-hexadecadienyl acetate (7)

To a reactor were charged (9E,11Z)-1-chloro-9,11-hexadecadiene (1-2: X=Cl) (75.4 g, 0.293 mol), sodium acetate (36.1 g, 0.440 mol), sodium iodide (6.16 g, 0.0441 mol) and N,N-dimethylacetamide (33.2 g), and the resulting mixture was stirred at 115 to 120° C. for 9 hours. After cooled to 10 to 15° C., water (322 g) and hexane (270 g) were added. After removal of the aqueous layer by liquid-liquid separation of the resulting reaction mixture, the organic layer was washed with a solution of sodium chloride (1.98 g) and water (43.4 g). It was concentrated by evaporating the solvent under vacuum, and the resulting concentrate was subjected to distillation under vacuum to obtain (9E,11Z)-9,11-hexadecadienyl acetate (7) (70.0 g, 0.250 mol) with a yield of 85.1%.

The invention claimed is:
1. A process for preparing (9E,11Z)-9,11-hexadecadienyl acetate of the following formula (7):

(7)

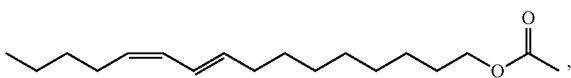

said process comprising at least steps of:
conducting a Wittig reaction between a (2E)-9-halo-2-nonenal of the following general formula (2-1):

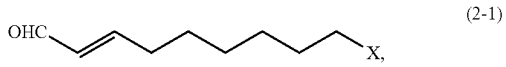
(2-1)

wherein X is a halogen atom, and a triarylphosphonium pentylide of the following general formula (3):

$$CH_3-(CH_2)_3-CH^--P^+Ar_3 \qquad (3),$$

wherein Ar may be the same or different at each occurrence and is an aryl group having 6 or 7 carbon atoms, to obtain a (7E,9Z)-1-halo-7,9-tetradecadiene of the general formula (1-1):

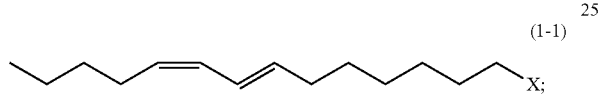
(1-1)

reacting the (7E,9Z)-1-halo-7,9-tetradecadiene (1-1) with magnesium to obtain a (7E,9Z)-7,9-tetradecadienyl magnesium halide;
subjecting the (7E,9Z)-7,9-tetradecadienyl magnesium halide to an addition reaction with ethylene oxide to obtain (9E,11Z)-9,11-hexadecadienol of the following formula (6):

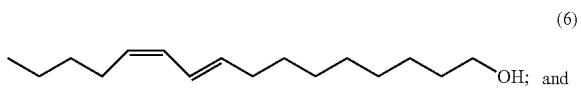
(6)

conducting an acetylation reaction of (9E,11Z)-9,11-hexadecadienol (6) with an acylating agent to obtain (9E,11Z)-9,11-hexadecadienyl acetate.

2. A process for preparing a 1-haloalkadiene of the following general formula (1A):

$$CH_3-(CH_2)_3-CH=CH-CH=CH-(CH_2)_{a'}-X \qquad (1A),$$

wherein X is a halogen atom, and a' is an integer of from 6 to 15,
said process comprising at least a step of:
conducting a coupling reaction of an alkadienyl magnesium halide derived from a 1-haloalkadiene of the following general formula (4):

$$CH_3-(CH_2)_3-CH=CH-CH=CH-(CH_2)_c-X^1 \qquad (4),$$

wherein $X^1$ is a halogen atom, and c is an integer of 3 or of from 5 to 12, with a dihaloalkane of the following general formula (5):

$$X-(CH_2)_d-X \qquad (5),$$

wherein X may be the same or different at each occurrence and is a halogen atom, and d is an integer of from 3 to 12, with a proviso that a sum of c and d is from 6 to 15, to obtain said 1-haloalkadiene.

3. The process for preparing the 1-haloalkadiene according to claim 2, wherein the 1-haloalkadiene of the general formula (4) is a (4E,6Z)-1-halo-4,6-undecadiene of the following general formula (4-1):

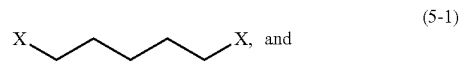
(4-1)

wherein $X^1$ is a halogen atom,
the dihaloalkane of the general formula (5) is a 1,5-dihalopentane of the following general formula (5-1):

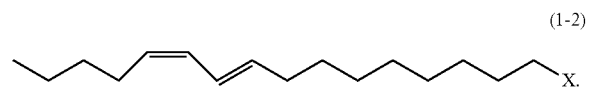
(5-1)

the 1-haloalkadiene of the general formula (1A) is a (9E,11Z)-1-halo-9,11-hexadecadiene of the following general formula (1-2):

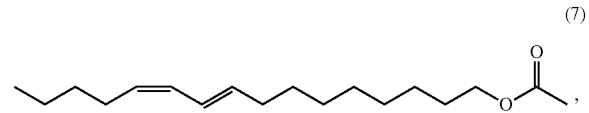
(1-2)

4. A process for preparing (9E,11Z)-9,11-hexadecadienyl acetate of the following formula (7):

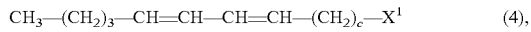
(7)

said process comprising at least steps of:
preparing the (9E,11Z)-1-halo-9,11-hexadecadiene of the general formula (1-2) by the process according to claim 3; and
substituting the halogen atom of the (9E,11Z)-1-halo-9,11-hexadecadiene (1-2) with an acetoxy group to obtain (9E,11Z)-9,11-hexadecadienyl acetate.

* * * * *